(12) United States Patent
Benard

(10) Patent No.: US 7,476,496 B2
(45) Date of Patent: Jan. 13, 2009

(54) METHOD FOR PREPARING AN EXTRACELLULAR MATRIX AND ITS USE FOR TUMOR CELL CULTURE

(75) Inventor: Jean Benard, L'Hay les Roses (FR)

(73) Assignee: Institut Gustave-Roussy (FR)

( * ) Notice: Subject to any disclaimer, the term of this patent is extended or adjusted under 35 U.S.C. 154(b) by 278 days.

(21) Appl. No.: 10/522,239

(22) PCT Filed: Jul. 28, 2003

(86) PCT No.: PCT/FR03/02376

§ 371 (c)(1),
(2), (4) Date: Nov. 7, 2005

(87) PCT Pub. No.: WO2004/011596

PCT Pub. Date: Feb. 5, 2004

(65) Prior Publication Data

US 2006/0099675 A1    May 11, 2006

(30) Foreign Application Priority Data

Jul. 26, 2002    (FR) .................................. 02 09525

(51) Int. Cl.
*C12N 5/02*    (2006.01)
*C12N 5/08*    (2006.01)
*C12N 5/06*    (2006.01)

(52) U.S. Cl. ............................. 435/4; 435/374; 435/375

(58) Field of Classification Search ........................ None
See application file for complete search history.

(56) References Cited

U.S. PATENT DOCUMENTS 6,383,805 B1    5/2002    Latimer

OTHER PUBLICATIONS

Nederman et al (Cancer Research, 1984, vol. 44, pp. 3090-3097).*
Abstract of Heldin et al. (Thryoidology, 1991, vol. 3, pp. 127-131).*
Nakamura et al.; Biosciences Information Service Abstract; "A Novel in Vitro Model System Simulating in Vivo Carcinoma Tissue"; FASEB Journal, Annual Meeting of the Professional Research Scientist on Experimental Biology, Apr. 20-24, 2002, vol. 16, No. 4, p. A472, (2002).
Gospodarowicz et al.; "Growth Factors and the Extracellular Martix"; Endocrine Reviews; vol. 1, No. 1, pp. 201-227, (1980).
Bénard et al.; "Characterization of Human Ovarian Adenocarcinoma Line, IGROV1, in Tissue Culture and in Nude Mice"; Cancer Research, vol. 45, pp. 4970-4979, (1985).

* cited by examiner

*Primary Examiner*—Karen A Canella
(74) *Attorney, Agent, or Firm*—Finnegan, Henderson Farabow, Garrett & Dunner, L.L.P.

(57) ABSTRACT

The invention concerns a method for preparing an isolated extracellular matrix, secreted by tumor cells, in particular epitheliomatous cells, methods for tumor cell culture using such a matrix, the use of such a matrix for producing a tumor cell line as well as novel tumor cell lines obtained by said method. The invention also concerns a method for selecting a compound capable of inhibiting the growth and/or proliferation of tumor cells, the use of said compounds as medicine for cancer treatment as well as a diagnosis or prognosis method in vitro by chromosomal analysis using said matrices. The invention further concerns a reactor or a kit for cell culture comprising such an extracellular matrix.

2 Claims, No Drawings

METHOD FOR PREPARING AN EXTRACELLULAR MATRIX AND ITS USE FOR TUMOR CELL CULTURE

The present invention relates to a method for preparing an isolated extracellular matrix (ECM) secreted by tumor cells, in particular epitheliomacus cells, to tumor cell culture methods using such a matrix, to the use of such a matrix for establishing a tumor cell line and also to novel tumor cell lines obtained by means of this method. The invention also relates to a method for selecting compounds capable of inhibiting the growth and/or the proliferation of tumor cells, to the use of such compounds as a medicinal product for the treatment of cancer, and also to a method of diagnosis or of prognosis, in vitro, by chromosome analysis using such matrices. The present invention also relates to a reactor or a kit for cell culture comprising such ECM.

Solid tumors, in particular epitheliomacus tumors, are difficult to culture and, where appropriate, to propagate in vitro in the form of lines. A solid cancerous tumor exhibits, besides its malignant epithelial contingent (cancerous cells in the strict sense), a contingent of stroma cells (fibroblasts, tumor vessel endothelial cells) without which the malignant cells cannot develop in vivo.

Whether it is a question of epithelia or of the support cells, all tissues organize and polarize from a basal laminar consisting of extracellular matrix (ECM), which is an assembly of integrins, of proteoglycan, of laminin proteins and of growth factor receptors. The composition and the structure of this ECM are specific for a given tissue.

Under the basal laminar, and in the case of an epithelium, the supporting connected tissue is made up of fibroblasts, macrophages, mast cells and endothelial cells from the vessels which feed this supporting tissue. Such a connected tissue synthesizes a very abundant ECM which allows it to respond to tensions, essentially mechanical tensions.

As regards the ECM of epithelia, it has a triple role:
maintaining the genes in their tissue context,
inducing morphogenesis after cell adhesion,
preventing apoptosis and tumor invasion (if there is a degradation phenomenon, the consequence is invasion).

The precise composition of the ECM of epithelial cells and of connective tissue cells is not known at the current time.

Among the reagents used to improve the adhesion of cancer cells to a support, mention may be made, for example of certain constituent proteins of extracellular matrix secreted by the basal laminar of an epithelium, such as laminin, collagen IV, or else gelatin, sold by many commercial laboratories. These reagents can be applied as a monolayer onto the plastic of culture flasks.

Mention may also be made of multiprotein complexes such as Matrigel® ("basal membrane-like") proposed by the company Sigma (USA). These complexes have an unknown composition and are generally extracted from experimental tumors after a cell lysis step.

Mention may also be made of the extracellular matrices derived from umbilical cord cells and sold by certain Academic University Laboratories.

Mention may also be made of fetal calf serum containing growth factors and adhesion factors, used in the cell culture medium, which promotes the adhesion of carcinoma cells.

In general, although these reagents promote the adhesion of cancerous cells, they do not make it possible to stimulate the proliferation of said cells or to stimulate said proliferation in a constant manner, due in particular to the variations in production batches and thus in their quality.

Finally, mention may be made of the technique for producing an extracellular matrix proposed by Gospodarowitcz et al. (Endocrine Reviews, 1(3): 201-227, 1980), from bovine cornea endothelial cells, used for tumor cell culture, this matrix inhibiting poor stability.

Thus, it remains to be able to provide a constant biological reagent for culturing malignant tumor cells that makes it possible to obtain both adhesion thereof, in particular on a plastic support, and proliferation thereof.

In fact, such reagents may be advantageously used not only for culturing tumor cells, but also for establishing tumor cell lines derived from a primary tumor. Such cultures or lines may be a tool of choice for studying their biological properties (nucleic acid, protein, enzyme activities), or else for carrying out tests for predicting tumor sensitivity to treatment (chemotherapy and radiotherapy).

It would also be desirable to be able to provide such reagents for a given type of cancer, allowing the proliferation of tumor cells derived from a sample of a tumor from a patient. In fact, the proliferation of such tumor cells or the establishment of a cell line from such cells would make it possible to study, in vitro and in the short term, the malignant cells from this patient and the sensitivity of these malignant cells to the treatment envisioned, before administration thereof to the patient.

This is precisely the subject of the present invention.

The inventors have demonstrated, surprisingly, that isolated extracellular matrices secreted by mammalian tumor cells, in particular epitheliomatous cells, make it possible to bring about the adhesion and proliferation of tumor cells, and make it possible to establish a tumor cell line established from tumor cells derived from a sample of a primary and/or metastatic tumor, in particular when these tumor cells, the culturing of which is being sought or for which the establishment of a cell line is being sought, are derived from a tissue having the same embryonic origin as the tumor cells secreting said matrix.

Thus, in a first aspect, a subject of the present invention is a method for preparing an isolated extracellular matrix secreted by tumor cells of animal origin, including human, characterized in that it comprises the following steps:
a) culturing said tumor cells of animal origin on a support under conditions that allow said tumor cells of animal origin to proliferate and to secrete said ECM; and
b) recovering the ECM thus formed, from which said tumor cells have been removed.

In a preferred embodiment, the method for preparing an isolated extracellular matrix according to the present invention is characterized in that it also comprises, between said step a) and said step b), the following step:
lysing said tumor cells.

In a particularly preferred embodiment, the method for preparing an isolated extracellular matrix according to the present invention is characterized in that said tumor cells of animal origin are epitheliomatous cells.

In an embodiment that is also preferred, the method for preparing an isolated extracellular matrix according to the present invention is characterized in that said tumor cells are cells of a tumor cell line pre-established from a primary tumor and/or from a metastatic proliferation.

Also preferably, the invention relates to a method for preparing an isolated extracellular matrix according to the present invention, characterized in that said tumor cell line has been established from tumor and/or metastatic cells derived from a mammary or ovarian tumor.

Even more preferably, the invention relates to a method for preparing an isolated extracellular matrix according to the present invention, characterized in that said tumor cells are cells derived from a tumor of human origin.

In a particularly preferred aspect, a subject of the invention is a method for preparing an isolated extracellular matrix according to the present invention, characterized in that said tumor cells are cells derived from the tumor cell line IGR-OV1 as deposited, under the conditions of the treaty of Budapest, with the Collection Nationale de Culture de Microorganismes (CNCM) [National Collection of Microorganism Cultures], Pasteur Institute, Paris (France), under the number I-2893, on Jun. 20, 2002.

The tumor cell line IGR-OV1 is a line of epitheloid cells derived from a primary tumor of a human ovarian cancer. These cancer cells develop as a monolayer and as "clusters" floating in the medium. These cell "clusters" are capable of adhering to plastic. On the other hand, the adherent cells can proliferate as floating "clusters" and it is the adherent contingent that is propagated (Bénard, J. et al., Cancer Research, 45, 4970-4979, 1985).

In a second aspect, a subject of the invention is an isolated extracellular matrix (ECM) that can be obtained by means of a method for preparing an isolated extracellular matrix according to the present invention.

Among the isolated ECMs according to the present invention, the isolated ECM secreted by the tumor cell line IGR-OV1 as deposited with the CNCM under the number I-2893 on Jun. 20, 2002, is most particularly preferred.

Preferably, the isolated ECM according to the present invention is packaged in a fluid, frozen, dried or lyophilized and, where appropriate, sterilized form.

In a third aspect, a subject of the invention is a reactor for cell culture containing an isolated ECM according to the present invention.

In a fourth aspect, a subject of the invention is a method for culturing tumor cells according to the present invention, characterized in that it comprises a step in which said tumor cells are brought into contact with an isolated ECM according to the present invention, said tumor cells that it is desired to culture being different from those from which said ECM was secreted.

In a fifth aspect, a subject of the invention is a method for preparing a tumor cell line established from tumor cells derived from a sample of a primary and/or metastatic tumor of animal, including human, origin, characterized in that said method implements a step in which the tumor cells contained in said sample of the tumor, and for which it is desired to obtain an established line, are brought into contact with an isolated ECM according to the present invention, said tumor cells for which it is desired to obtain an established line being different from those from which said ECM was secreted.

In a preferred embodiment, the method for culturing tumor cells according to the present invention or the method for preparing a tumor cell line according to the present invention is characterized in that the first tumor tissue from which are derived the tumor cells from which said ECM was obtained, and the second tumor tissue containing the tumor cells that it is desired to culture or for which it is desired to establish a cell line, are the same animal species, including humans.

In an embodiment that is also preferred, the method for culturing tumor cells according to the present invention or the method for preparing a tumor cell line according to the present invention is characterized in that said first tumor tissue and said second tumor tissue are derived, independently of one another from the group of malignant or benign tumors, in particular derived from ovarian, breast, prostate or thyroid tumors.

Also preferably, the method for culturing tumor cells according to the present invention or the method for preparing a tumor cell line according to the present invention is characterized in that said first tumor tissue is a tissue derived from a breast tumor, in particular from the tumor cell line IGR-OV1, and said second tumor tissue is derived from malignant or benign ovarian tumors, breast tumors, prostate tumors or thyroid tumors.

In an embodiment that is also preferred, the method for culturing tumor cells according to the present invention or the method for preparing a tumor cell line according to the present invention is characterized in that said first tumor tissue and said second tumor tissue are of the same embryonic origin.

The term "same embryonic origin" for a tumor tissue is intended to denote, in the present description, tumor tissues that derive from the same embryonic primary tissues (endoderm, ectoderm or mesoderm). For example, ovarian and mammary epitheliomatous tumors will be considered as being derived from the same embryonic origin since ovarian and mammary epithelial tissues derive from the endoderm.

In an embodiment that is also preferred, the method for culturing tumor cells according to the present invention or the method for preparing a tumor cell line according to the present invention is characterized in that said first tumor tissue and said second tumor tissue are of different embryonic origin, preferably derived from the endoderm and from the ectoderm, or vice versa.

In an embodiment that is also preferred, the method for culturing tumor cells according to the present invention or the method for preparing a tumor cell line according to the present invention is characterized in that said first tumor tissue and said second tumor tissue are, independently of one another, of mammary or ovarian type.

In a more preferred embodiment, the method for culturing tumor cells according to the present invention or the method for preparing a tumor cell line according to the present invention is characterized in that said first tumor tissue is of ovarian type and said second tumor tissue is of mammary or ovarian type.

In a particularly preferred aspect, a subject of the invention is a method for culturing tumor cells according to the present invention or a method for preparing a tumor cell line according to the present invention, characterized in that said first tumor tissue and said second tumor tissue are of human origin.

In a sixth aspect, a subject of the invention is the use of an isolated ECM according to the present invention, as an element of a culture medium for the cell culture of tumor cells, or for the establishment of a cell line of tumor cells, derived from a primary tumor and/or from a metastatic proliferation, said tumor cells being different from those from which said ECM was secreted.

In a seventh aspect, a subject of the invention is an established tumor cell line obtained by means of a method for preparing a tumor cell line according to the present invention.

Among the established tumor cell lines that can be obtained by means of a method for preparing a tumor cell line according to the present invention, preference is most particularly given to the tumor cell line called IGR-OV-22-AS as deposited, under the conditions of the treaty of Budapest, with the CNCM Institut Pasteur, 25 Rue du Docteur Roux, Paris, France under the number I-2894 on Jun. 20, 2002, or the tumor cell line called IGR-BR-11-NS as deposited, under the conditions of the treaty of Budapest, with the CNCM under the number I-2895 on Jun. 20, 2002.

The tumor cell line called IGR-OV-22-AS was established from epitheliomatous cells contained in a sample of carcinomatus peritoneal ascites from a human ovarian epithelial adenocarcinoma and in a genetic context of predisposition to breast and/or ovarian cancer syndrome, the ovarian epithelial cancer having developed in a patient constitutionally heterozygote for the BRCA2 gene (mutation of one allele of the gene). These epitheliomatous cancer cells develop as a monolayer.

Human breast cancer, epitheliomatous cells derived from a nodule.

The tumor cell line called IGR-BR-11-NS was newly established in a genetic context of predisposition to breast/ovarian cancer syndrome, in a patient heterozygote for BRCA1 (mutated for one allele of the gene).

These epitheliomatous cancer cells also develop as a monolayer.

In an eighth aspect, a subject of the invention is a method for selecting a compound capable of inhibiting the growth and/or the proliferation of tumor cells, characterized in that it comprises the following steps:

a) culturing said tumor cells, this comprising at least one step of culturing on an isolated ECM according to the present invention, said tumor cells being different from those from which said ECM was secreted;

b) bringing said compound into contact with the tumor cells obtained in step a), under conditions that normally allow their growth and/or their proliferation; and c) selecting said compound if it is capable of inhibiting the growth and/or the proliferation of said tumor cells.

In a preferred embodiment, the method for selecting a compound according to the present invention is characterized in that said isolated ECM in step a) is the ECM secreted by the tumor cell line IGR-OV1 as deposited with the CNCM under the number I-2893 on Jun. 20, 2002.

In a more preferred embodiment, a subject of the invention is a method for selecting a compound capable of inhibiting the growth and/or the proliferation of tumor cells, in particular of tumor cells from an ovarian tumor, preferably human, or of tumor cells of the same embryonic origin as an ovarian cell, characterized in that it comprises the following steps:

a) bringing said compound into contact with a cell culture derived from the tumor cell line IGR-OV-22-AS as deposited with the CNCM under the number I-2894 on Jun. 20, 2002; and b) selecting said compound if it is capable of inhibiting the growth and/or the proliferation of said tumor cells.

In an embodiment that is also more preferred, a subject of the invention is a method for selecting a compound capable of inhibiting the growth and/or the proliferation of tumor cells, in particular of tumor cells from a mammary tumor, preferably human, or of tumor cells of the same embryonic origin as a mammary cell, characterized in that it comprises the following steps:

a) bringing said compound into contact with a cell culture derived from the tumor cell line of human origin IGR-BR-11-NS as deposited with the CNCM under the number I-2895 on Jun. 20, 2002; and b) selecting said compound if it is capable of inhibiting the growth and/or the proliferation of said tumor cells.

In an embodiment that is also more preferred, a subject of the invention is a method for selecting a compound capable of inhibiting the growth and/or the proliferation of tumor cells from a patient suffering from a tumor, using a sample of tumor cells taken beforehand from said patient, characterized in that it comprises the following steps:

a) establishing a tumor cell line from said tumor cells taken from the patient by means of a method for preparing an established tumor cell line by means of a method according to the present invention;

b) bringing said compound into contact with a sample of the tumor cell line obtained in step a), under conditions that normally allow its growth and/or its proliferation; and c) selecting said compound if it is capable of inhibiting the growth and/or the proliferation of the cells of the tumor cell line.

In a ninth aspect, a subject of the invention is the use of a compound for preparing a medicinal product intended for the treatment of a cancer, characterized in that said compound is selected by means of a method of selection according to the present invention.

Preferably, the invention relates to the use of a compound according to the present invention, for preparing a medicinal product intended for the treatment of breast cancer or ovarian cancer.

In a tenth aspect, a subject of the invention is a method of diagnosis or of prognosis, in vitro, by chromosomal analysis, in particular by cytogenetic and interphase FISH analysis, of tumor cells taken beforehand from a patient, characterized in that it comprises a step in which said tumor cells, taken beforehand, that it is desired to test are cultured on an isolated ECM according to the present invention, said tumor cells being different from those from which said ECM was secreted.

In a preferred embodiment, the method of diagnosis or of prognosis, in vitro, by chromosomal analysis of tumor cells taken beforehand from a patient is characterized in that it comprises the following steps:

a) establishing a tumor cell line from said tumor cells by means of a method for preparing an established tumor cell line by means of a method according to the present invention; and b) chromosomal analysis of a sample of cells of said line obtained in step a), under conditions that allow their growth and/or their proliferation; and c) demonstrating a genetic alteration of one or more chromosomes by means of a technique for detecting such alterations, in particular by karyotype analysis or by the "interphase FISH" technique.

The genome of tumor cells is characterized by a set of genetic alterations: gain and/or loss of chromosomal regions. A cytogeneticist routinely reveals these alterations by means in particular of two techniques: karyotype analysis and FISH ("Fluorescent In Situ Hybridization") analysis, techniques well known to those skilled in the art, for which only certain steps are recalled here in order to note the importance of being able to have tumor cells that possess a proliferative capacity.

Karyotype Analysis After In Vitro Culture of Tumor Cells.

Twenty-four hours after seeding of the tumor cells, a solution of colchicine is added to the culture medium. The cells which are adhered to the plastic and which have begun to proliferate will be blocked in mitosis, thus revealing their chromosomes. The yield of mitoses under these conditions is very variable according to the type of tumor and the proliferative capacity of the tumor tissue.

Interphase FISH Analysis on Cell Appositions

The apposition of a tumor fragment on a slide for cytological observation enables malignant cells to be deposited and, after fixing, analysis by fluorescent in situ hybridization. This analysis does not require cells undergoing mitosis, but applies to all cells, the majority being in interphase, a small minority therefore undergoing mitosis makes it possible to visualize the chromosomes.

The epitheliomatous tumor cells in the presence of extracellular matrix according to the invention, in particular derived from the IGR-OV1 line, will adhere, differentiate and proliferate. Thus, according to the technique used by the cytogeneticist for revealing the genetic alterations of tumor cells, the extracellular matrix of the invention introduces the following improvements.

For the Karyotype Analysis

The karyotype analysis requires a prior cell culture in order to recruit cells undergoing mitoses. These cultures are usually effected on a plastic support, which does not promote in particular the adhesion and the proliferation of epitheliomatous cancer cells. The yield of the analysis is very low due to a limited number of mitoses. Since culturing in the presence of extracellular matrix according to the invention promotes adhesion specific to tumor cells and their proliferation, the number of mitoses of tumor cells recruited by the matrix will be much greater.

For the FISH Analysis

On a slide exhibiting the pre-prepared extracellular matrix, the presence of the extracellular matrix according to the invention fixed on the slide allows increased adhesion of the cancer cells. The tumor footprints produced on the matrix will be richer in cells and will reduce the analysis time.

In a final aspect, a subject of the invention is a kit for culturing tumor cells, in particular derived from a mammary or ovarian tumor, or for establishing a cell line derived from said tumor cells, comprising an ECM according to the invention.

The present invention also relates to a solid support, in particular a glass slide, on which is fixed an extracellular matrix according to the present invention, and to its use for the chromosomal analysis of tumor cells.

The following examples were chosen so as to provide those skilled in the art with a complete description in order to be able to produce and use the present invention. These examples are not intended to limit the scope of what the inventors consider to be their invention, nor are they intended to show that only the experiments below were carried out.

EXAMPLES

Example 1

Preparation of an Extracellular Matrix Obtained from the IGR-OV1 Line

1) Culturing of the IGR-OV1 Cells

The IGR-OV1 cells (doubling time approximately 25 h) are cultured between passages 170 and 210 corresponding to approximately 500 generations, the number of generations guaranteeing stability of the line. Once confluency has been reached, the cells are split 1-in-3 in 25 $cm^2$ culture flasks, and cultured in 5 ml of RPMI 1640 supplemented with 10% of fetal calf serum. After 3 days of culture in an incubator at 37° C. in the presence of 5% $CO_2$, the epitheliomatous cells reach confluency.

2) Preparation of the Matrix

The culture medium covering the confluent cells is removed and replaced with calcium and magnesium free PBS buffer (phosphate buffer saline) preincubated at 37° C. This operation is repeated 3 times, it makes it possible to remove the proteins of the culture medium, the presence of which would alter the reproducibility of the cell lysis. The volumes of the 3 successive buffers are as follows:

1 ml per well of a 24-well plate,
2 ml per well of a 6-well plate,
5 ml for a 25 $cm^2$ culture flask,
10 ml for 75 $cm^2$ culture flask.

After the third settling out of the PBS, the same volume of 0.02 M $NH_4OH$, preheated to 37° C., is poured over the walls of the flask before being applied to the confluent cells. The incubation is carried out in a $CO_2$ incubator at 37° C. for 6 minutes. If, at the end of this incubation time, the lysis is not complete, it is continued in 30-second segments. When all the cell bodies have disappeared, the process is stopped by settling out of the ammonia-containing solution, which is very viscous (genomic DNA released by the cells). The matrix is washed by means of a cycle of addition-settling out, repeated 3 times, with the same volume of PBS as the lysis volume. The first wash may still be viscous. The washes must be effective but sufficiently gentle so as not to damage the matrix.

3) Conservation of the Matrix

The culture flasks and plates containing the matrix are conserved in heat-sealed bags in ¼ of the culture volume of a PBS medium containing antibiotics, the entire assembly being placed at 4° C. The matrix thus prepared can be used between the 3rd and the 21st day following its preparation, without degradation.

4) Required Material and Media

Material:
  Costar culture plates (6-well, 24-well and 96-well dish);
  Nunc 25 and 75 $cm^2$ culture flasks.

Culture Media:
  Gibco BRL RPMI 1640, supplemented with:
    2 mM glutamine,
    antibiotics: vancomycin (12 µg/ml), gentamycin (10 µg/ml) and fungizone (2 µg/ml).
  The medium thus reconstituted is buffered with the final concentration of 10 mM of Hepes.
    Fetal calf serum of Canadian origin, from the company Biomedia;
    PBS (PBS stands for "Phosphate Buffer Salts"), calcium and magnesium free, Gibco;
    matrix conservation medium: Gibco calcium and magnesium free PBS in the presence of antibiotics and at the final concentration indicated above.

Example 2

Production of Two Epitheliomatous Lines: IGR-OV-22 and IGR-BR-11

A) Establishing the Epitheliomatous Line IGR-OV-22

Cancer of the ovarian epithelium develops in the form of a locoregional solid ovarian tumor and of a peritoneal ascites containing epitheliomatous cells.

The primary tumor (TP) and the ascites (Asc) taken beforehand from a patient with a family context of susceptibility to breast and/or ovarian cancer, which patient was constitutionally heterozygote for the BRCA2 gene, were received by the anatomy-pathology laboratory.

1) Preparation of the Tumor

Punctures were made in the tumor using a needle (22 gauge) and a 1 ml pre-heparinized syringe (insulin type). The content of the syringe was taken up in a large volume of RPMI 1640-10% fetal calf serum, and then centrifuged. The red blood cells contaminating the cell pellet were removed by hypotonic shock using sterile distilled water. The cell suspension was again centrifuged and, finally, taken up in 4 ml of RPMI 1640-10% fetal calf serum, which made it possible to obtain a suspension of epitheliomatous cells at $7.5 \times 10^5$ cells/ml. The cell suspension thus prepared was seeded into the 12 wells of a culture plate exhibiting the extracellular matrix secreted by the IGR-OV1 line prepared beforehand (matrix prepared 17 days previously). The seeding density is high, approximately $3 \times 10^5$ cells/4.5 cm².

2) Preparation of the Ascites

A large volume of sampled ascites was centrifuged in the presence of RPMI 1640-10% fetal calf serum. The cell population pellet obtained was then treated under the same conditions as those described above for the tumor. The epitheliomatous cells were seeded in a 24-well plate exhibiting the extracellular matrix secreted by the IGR-OV1 line, using the same cell concentrations indicated above.

3) In Vitro Culturing of the Epitheliomatous Cells from the Tumor and from the Ascites Observation of the cultures every four days made it possible to objectify epitheliomatous cells adhering to the substrate, differentiating (in view of their morphology) and proliferating.

When confluence was observed, the cells were trypsinized with 0.025% trypsin-EDTA, taken up in the RPMI 1640 medium—10% fetal calf serum, and re-seeded onto matrix at the same initial seeding densities.

After amplification of the two cell populations, TP and Asc, in 12-well culture dishes for 5 passages, the subsequent 5 passages were carried out in culture flasks with a greater culture surface area, i.e. 25 cm², again exhibiting the extracellular matrix.

At the end of these 10 passages on extracellular matrix, the epitheliomatous cells are capable of propagating directly on plastic. Since the TP and Asc tumor cells have undergone 20 passages, the sublines IGR-OV22-Asc and IGR-OV22-TP are considered to be established, exhibiting a similar and typically epitheliomatous tumor phenotype.

B) Establishing the IGR-BR-11 Line

The primary tumor (TP) of a mammary cancer taken beforehand from a patient with a familial context of susceptibility to breast and/or ovarian cancer, which patient is constitutionally heterozygote for the BRCA1 gene, was received by the anatomy-pathology laboratory.

The protocol indicated for establishing the IGR-OV-22 (TP) line, in particular the initial seeding concentrations, was strictly identical for establishing this IGR-BR-11 line. At the end of 10 passages in the presence of extracellular matrix, the epitheliomatous cells were cultured for 30 passages on plastic in the absence of extracellular matrix. The IGR-BR-11 line was thus established.

Example 3

Culture of Epithelial Tumor Cells of Various Histological Types and of Variable Malignancy Using the ECM Derived from the Tumor Cell Line IGR-OV1

Primary culturing (P0) initiated on the ECM derived from the tumor cell line IGR-OV1, followed by successive passages (P1, P2, etc.) were successfully carried out with cells derived from:

A) Malignant Tumors

1) Cancerous breast tumors (n=8)
Results:
two P0s, each followed by P1; and
one established line (P40).

i.e. a success score of ⅜ (35%).

2) Cancerous ovarian tumors (n=5)
Results:
three P0s; and
one P0, followed by P1, P2, P3 and P4.

i.e. a success score of ⅘ (80%).

3) Cancerous prostate tumors (n=2)
one P0, followed by P1 and P2.

i.e. a success score of ½ (50%).

4) Papillary thyroid cancers (n=2)
two P0s, each followed by P1.

i.e. a success score of 2/2 (100%).

B) Tumors with Border-Line Malignancy and Benign Tumors

1) "Border-line" ovarian tumor (n=7)
three P0s followed by P1; and
two P0s.

i.e. a success score of 5/7 (70%).

2) Thyroid goiter (n=1)
one P0.

i.e. a success score of 1/1 (100%).

Thus, primary cultures of cancerous epithelial cells were successfully realized on ECM, not only for the following various malignant tumors: breast, ⅜ (35%), ovarian ⅘ (80%), prostate ½ (50%), thyroid 2/2 (100%); but also on ovarian tumors with border-line malignancy, 5/7 (70%), and benign thyroid tumors, 1/1 (100%).

These results therefore indicate the advantage of the ECMs according to the present invention, the IGR-XC matrix, for culturing epithelial tumors of various histological types and of variable malignancy (16/25, i.e. 65%), and also for establishing new cell lines.

The invention claimed is:

1. A method for selecting a compound capable of inhibiting the growth and/or the proliferation of tumor cells comprising:
   a) bringing said compound into contact with a cell culture comprising the tumor cell line IGR-OV-22-AS as deposited with the Collection Nationale de Cultures de Microoranismes (CNCM) under accession number I-2894 or comprising the tumor cell line of human origin IGR-BR-11-NS as deposited with the CNCM under accession number I-2895; and
   b) selecting said compound if it is capable of inhibiting the growth and/or the proliferation of said tumor cells.

2. The method of claim 1, wherein the cell culture is produced by culturing the tumor cell line IGR-OV-22-AS or tumor cell line of human origin IGR-BR-11-NS.

* * * * *